US007927884B2

(12) United States Patent
Sullivan et al.

(10) Patent No.: US 7,927,884 B2
(45) Date of Patent: Apr. 19, 2011

(54) SYSTEMS AND METHODS FOR DETERMINING CARBON CREDITS

(76) Inventors: Leigh Albert Sullivan, Lismore (AU); Jeffrey Francis Parr, Lismore (AU)

( * ) Notice: Subject to any disclaimer, the term of this patent is extended or adjusted under 35 U.S.C. 154(b) by 815 days.

(21) Appl. No.: 11/661,442

(22) PCT Filed: Jul. 29, 2005

(86) PCT No.: PCT/AU2005/001117
§ 371 (c)(1),
(2), (4) Date: Aug. 7, 2007

(87) PCT Pub. No.: WO2006/024070
PCT Pub. Date: Mar. 9, 2006

(65) Prior Publication Data
US 2008/0131974 A1     Jun. 5, 2008

(30) Foreign Application Priority Data

Aug. 30, 2004   (AU) .............................. 2004904928
Nov. 16, 2004   (AU) .............................. 2004906538

(51) Int. Cl.
*G01N 33/00*  (2006.01)
*A01H 3/00*   (2006.01)
*G01N 1/00*   (2006.01)
(52) U.S. Cl. .................. 436/145; 73/863; 47/58.1 R
(58) Field of Classification Search .................. None
See application file for complete search history.

(56) References Cited

FOREIGN PATENT DOCUMENTS
AU         2003/235033         2/2005

OTHER PUBLICATIONS

Parr, J.F., and Sullivan, L.A., Soil carbon sequestration in phytoliths., Soil Biology and Biochemistry (Jan. 2005) vol. 37, pp. 117-124.
Conley, D.J., Terrestrial ecosystems and the global biogeochemical silica cycle, Global Biogeochemical Cycles (2002) vol. 16, No. 4, 1121, pp. 68-1-68/8.
Parr, J.F. et al., A Comparative Analysis of Wet and Dry Ashing Techniques for the Extraction of Phytoliths from Plant Material, Journal of Archaeological Science, vol. 28, No. 8, Aug. 2001 pp. 875-886.
Parr, J.F. et. al., A Microwave Digestion Method for the Extraction of Phytoliths from Herbarium Specimens, Review of Palaeobotany and Palynology, vol. 116, No. 3-4, Sep. 2001, pp. 203-212.
West, T. et al., "Soil Organic Carbon Sequestration Rates by Tillage and Crop Rotation: A Global Data Analysis", Soil Sci, Soc. Am. J., vol. 66, Nov.-Dec. 2002, pp. 1930-1946.
Kelly, E. et al., "Stable Isotope Ratios of Carbon in Phytoliths as Quantitative Method of Monitoring Vegetation and Climate Change", Quaternary Research 35: pp. 222-233 (1991).

*Primary Examiner* — Jill Warden
*Assistant Examiner* — Neil Turk
(74) *Attorney, Agent, or Firm* — Greer, Burns & Crain, Ltd.

(57) ABSTRACT

A method for determining the phytolithic organic carbon yield of a plant type at a location or region comprising: a) taking a sample of a plant type growing in the location or region; b) quantifying phytolithic organic carbon in the sample; c) quantifying a total biomass of the plant type growing at the location or region; and d) determining a total amount of phytolithic organic carbon for the total biomass of the plant type at the location or region.

12 Claims, No Drawings

SYSTEMS AND METHODS FOR DETERMINING CARBON CREDITS

FIELD OF THE INVENTION

The present invention relates to systems and methods for determining carbon credits. The invention also relates to methods for determining carbon sequestration. The present invention also relates to methods for trading carbon credits.

BACKGROUND TO THE INVENTION

The threat of global warming has caused increasing alarm, both scientific and public, over the past two decades. Although debate is ongoing, a number of leading environmental scientists believe that global warming is a result of increased level of carbon dioxide and other greenhouse gases in the atmosphere. Studies have shown that atmospheric carbon dioxide levels in the late 1950s were around 315 ppm and have been rising ever since. Recent data has shown that the carbon-dioxide levels in the atmosphere had risen to about 376 ppm at the end of 2003.

The increased levels of atmospheric carbon dioxide have been attributed largely to increased burning of fossil fuels.

As a result of growing concern over the potentially devastating effects of global warming, the United Nations Framework Convention on Climate Change (UNFCCC) was adopted in 1992. By June 1993, the convention had received signatures from 166 countries. The Kyoto protocol, which is a protocol to the UNFCCC, was adopted at the third session of the conference of the parties to the UNFCCC in Kyoto, Japan, on 11 Dec. 1997. The provisions of the Kyoto protocol attempt to regulate the output of carbon dioxide by member states that have signed and ratified the protocol. Although a large number of countries have agreed to be bound by the provisions of the Kyoto protocol, neither Australia nor the United States of America are yet to ratify the protocol.

The levels of atmospheric carbon dioxide are controlled by two factors, these being (a) the amount of carbon dioxide being emitted into the atmosphere and (b) the amount of carbon dioxide being removed from the atmosphere into carbon sinks. Carbon sinks act as reservoirs for storing carbon dioxide. Carbon sinks may include biomass (such as forest and crops), plankton, soils, water bodies and geosequestration sinks. Thus, the net carbon dioxide emissions of any particular country are calculated by determining total carbon dioxide emissions and total carbon dioxide taken up by carbon sinks.

The UNFCCC allows for a system of carbon trading. Under this system, parties who establish carbon sinks obtain a "carbon credit" in respect of the amount of carbon dioxide taken up into the carbon sinks. This carbon credit can be traded to greenhouse gas emitters in order to enable the emitters to meet their targets under the Kyoto protocol.

It is known that as a result of plant growth, carbon based materials form in a plant structure and the carbon based materials may return to the soil to form carbon-containing deposits. There is established methodology to determine soil organic carbon content, which is a factor of interest to those managing agricultural businesses. Most organic material that is returned to the soil eventually rots and its carbon content is emitted over a period of time as that material rots away.

Phytoliths, also referred to as plant opal, are silica features that form in plants as a result of biomineralisation. Silica that occurs within soils is taken up by the root system of a plant in the form of silicic acid ($SiOH_4$), and subsequently deposited throughout the intra cellular and extra cellular structures of their leaf, stem and root systems. Piperno (1988), Phytolith Analysis: "An Archaeological and Geological Perspective" (Academic Press London) describes three sites of silica deposition within plant tissue. The sites comprise (1) the cell wall deposits, often called membrane silicification, (2) infillings of the cell lumen, and (3) in intercellular spaces of the cortex. The cell wall deposits often replicate the morphology of the living cells, while those forming in the lumen do not.

The presence of carbon within phytoliths was first discussed by the Australian CSIRO scientists Jones and Milne (1963) "Studies of Silica in the Oat Plant", Plant and Soil XVIII(2):207 220. Following this initial research, a number of studies on carbon in fossil phytoliths were undertaken. Such studies have concentrated on radiocarbon dating of fossil phytoliths to establish stratigraphic chronologies for archaeological and palaeobotanical research or δ13C isotope values to determine palaeovegetation types based on C3 and C4 signatures. The presence of organic carbon in phytoliths has been recognised for its role in radiocarbon dating. Radio carbon dating has been conducted by the inventors and it has been demonstrated that the carbon occluded within phytoliths in a soil depth of up to around 1.2 m was in the order of 8,000 years old. The inventors' studies do not explore to a limit position sequestration of carbon in phytoliths but there is no evidence to suggest that there would be appreciable carbon release over much longer periods of phytolithic storage under most soil conditions.

It is also known that phytoliths can be separated from other organic fractions by heavy liquid flotation (for example, using a specific gravity of 2.35 $gcm^{-3}$) or, as reported by one of the present inventors (i.e. Parr), acid digestion of the organic and carbonate component, thus leaving a silica residue (see one of the inventor's (i.e. Parr) publication "A composition of heavy liquid floatation and microwave digestion techniques for the extraction of fossil phytoliths from sediments." Review of Palaeobotany & Palynology, 120 (2002): 315-336).

BRIEF DESCRIPTION OF THE INVENTION

In a first aspect, the present invention provides a method for determining the phytolithic organic carbon yield of a plant type at a location or region comprising:

a) taking a sample of a plant type growing in the location or region;

b) quantifying phytolithic organic carbon in the sample;

c) quantifying a total biomass of the plant type growing at the location or region; and d) determining a total amount of phytolithic organic carbon for the total biomass of the plant type at the location or region.

The method of the first aspect of the present invention allows for the quantification of the phytolithic organic carbon yield of a particular plant type growing at a location or region. In this method, a sample of the plant type is collected from the location or region. The sample may comprise a single example of the plant type or, more preferably, it may comprise a number of specimens of the plant type. The sample is then analysed to determine the phytolithic organic carbon content of the sample. The phytolithic organic carbon content of the sample may be determined by any suitable process. For example, the sample may be subjected to low temperature combustion, to acid digestion or to microwave digestion.

Parr, J. F., Lentfer, C. J. and Boyd, W. E., (2001) "A comparative analysis of wet and dry ashing techniques for the extraction of phytoliths from plant material." Journal of Archaeological Science 28: 875-886 and Parr, J. F., Dolic, V., Lancaster, G. and Boyd, W. E., (2001) "A microwave digestion method for the extraction of phytoliths from herbarium specimens." Review of Palaeobotany and Palynology, 116 (2001): 203-212, both describe several methods for extracting phytoliths from plants. The entire contents of these articles are herein incorporated by cross reference.

Once the phytoliths have been extracted from the sample, the phytoliths can be analysed to determine their carbon content (hereinafter referred to as phytolithic organic carbon or PhytOC) and thus the phytolithic organic carbon content of the sample determined.

The carbon content of the extracted phytoliths can be determined by a number of methods known to the skilled person. The present inventors have also uniquely used a LECO carbon analyser instrument to determine the carbon content of the extracted phytoliths.

Measurement of the carbon content of the phytoliths, often after description of the phytoliths, usually involves organic carbon determination, using the LECO instrument, dichromate digestion or other suitable method.

The method of the first aspect of the present invention also involves quantifying the total biomass of the plant type at the location or region.

The total biomass of the plant type can be determined by a number of different methods known to be suitable by the person skilled in the art. These methods may include:
  direct sampling;
  indirect measurement using harvest data and known harvest indices;
  remote sensing techniques; and
  using appropriate biomass accumulation curves (see, for example, Montague et. al, "Carbon Sequestration Predictor for Land Use Change in Inland Areas of New South Wales—Background User Notes, Assumptions and Preliminary Model Testing, Version 2.0.", Research and Development Division State Forests of New South Wales, Sydney 2003).

The skilled person will readily recognise and understand that the above methods and other methods may be used to determine the total biomass of the plant type growing at the location or region and further description of such methods need not be provided.

Once the phytolithic organic carbon content of the sample has been determined and the total biomass of the plant type has also been determined, the total amount of phytolithic organic carbon present in the plant type growing at the location or region can be simply calculated. It will be appreciated that steps (b) and (c) may be conducted in any order.

If mixed vegetation is growing at the location or region, the method of the first aspect of the present invention preferably involves taking a sample of one or more, preferably all, plant types growing at the location or region, determining the phytolithic organic carbon contents for each of the samples of plant types, quantifying the total biomass of each of the plant types growing at the location or region and determining the total amount of phytolithic organic carbon.

The carbon present in phytoliths remains sequestered within the phytolithic structure for a long period of time, in excess of several thousand years. The present inventors have realised that phytoliths provide an opportunity to sequester carbon. The present inventors have further realised that this provides an opportunity to obtain carbon credits by virtue of carbon becoming locked up in phytolithic structures.

Accordingly, in a second aspect, the present invention provides a method for determining a carbon credit including the steps of:
  a) taking a sample of a plant type growing in a location or region;
  b) quantifying phytolithic organic carbon in the sample;
  c) quantifying a total biomass of the plant type at the location or region;
  d) determining a total amount of phytolithic organic carbon for the total biomass of a plant type at the location or region; and
  e) determining a carbon credit applicable to the location or region based upon the total amount of phytolithic organic carbon determined in step (d) above.

The carbon credit determined in the method of the second aspect of the present invention arises because the phytolithic organic carbon content of the particular plant types growing at the location or region represents carbon that is essentially permanently sequestered in the phytolithic structures. Thus, the phytolithic organic carbon is largely non-biodegradable and represents carbon that has been essentially removed from the atmosphere for millennia. The carbon credit calculated according to this aspect of the present invention claims a credit for all carbon sequestered in the phytoliths.

If the location or region is subjected to cultivation or agriculture, in which crops of the plant type are periodically grown at regular intervals (e.g. one crop every year), the total phytolithic organic carbon present in the crop represents a cumulative total of carbon permanently sequestered from the atmosphere for each cropping cycle. Thus, a carbon credit equivalent to the phytolithic organic carbon total of the crop minus that which would have been sequestered had the crop not been cultivated can be claimed for each cropping cycle.

If the location or region is not subjected to regular cropping, the increase in biomass on the location or region due to plant growth over a period of time can be claimed as a carbon credit. In this regard, it will be understood that as the plants growing on the location or region produce greater above ground biomass, the amount of phytolithic organic carbon in the plants will increase. This increase represents a carbon credit that can be determined in accordance with the method of the present invention.

It is also possible to determine phytolithic organic carbon arising from a particular plant type growing at a region or location by analysing soil. In this regard, different plant types (including different plant families and different plant species) have been found to have phytolith types that do not overlap in morphology with each other.

According to a third aspect, the present invention provides a method of providing data relating to carbon sequestration comprising:
  a) taking a soil sample at a selected location where a plant type has grown or is growing;
  b) isolating phytoliths from the sample;
  c) quantifying phytolithic organic carbon in the sample from the plant type to provide data; and
  d) providing a projection for the data to support a carbon credit claim for the plant type growing at the location.

Step (c) may comprise a microscopic assessment of the phytoliths to correlate them with phytolithic structures derived from the plant type of interest. The phytoliths may be isolated from the soil by using a flotation method, such as a dense medium flotation. Alternatively, phytoliths may be isolated from the soil by a microwave digested method pioneered by one of the inventors Parr (2002) to remove soil and degradable organic carbon from the soil sample to leave a residue containing the phytoliths, see Parr, J. F. (2002) "A comparison of heavy liquid floatation and microwave digestion techniques for the extraction of fossil phytoliths from sediments." Review of Palaeobotany and Palynology 120 (3-4): 315-336. The entire contents of this reference are herein incorporated by cross reference.

The methods of the second aspect and third aspect of the present invention both provide methods for providing data to support a claim for a carbon credit. The second aspect utilises an analysis of a sample of a plant type to provide the necessary data whereas the third aspect utilises an analysis of the soil to obtain the determination of the phytolithic organic carbon content of plant types growing at the location.

It may also be possible to determine the amount of phytoliths produced at a location by analysing the phytolith content of material recovered from the ground at the location. By determining phytolith content of the material on the ground at the location at spaced intervals, it is possible to determine the amount of phytolithic material added to the material during the interval of time. Thus, in a fourth aspect, the present invention provides a method for determining the phytolithic organic carbon accumulating at a location over a period of time comprising the steps of:

a) collecting a sample of material from the ground at the location;

b) determining the phytolithic organic carbon content of the material;

c) using data determined in step (b) above, determining a total phytolithic organic carbon content in the material at the location;

d) after a predetermined period of time has elapsed, collecting a further sample of material from the ground at the location;

e) determining a phytolithic organic carbon content of the material in the sample;

f) determining a total phytolithic organic carbon content in the material at the location from the data determined in step (e) above; and g) determining an amount of phytolithic organic carbon that has accumulated at the location over the predetermined time interval by subtracting the amounts determined in step (c) from the amount determined in step (f).

The method of the fourth aspect of the present invention determines the amount of phytolithic organic carbon material present on the ground (such as in the soil) at the start of a time interval. At the end of a predetermined time interval, typically one year later (which correlates to a growing cycle of plant types growing at the location), the phytolithic organic carbon content in the material collected from the ground is again determined. As plants growing at the location during the predetermined time interval are likely to have deposited phytolithic material onto the ground during that time interval, the phytolithic organic carbon present in material collected in the ground should have increased. The method of the fourth aspect of the present invention measures that increase.

The material collected from the ground preferably includes leaf litter, humus and at least an upper layer of the soil.

In a fifth aspect, the present invention provides a method for sequestering carbon comprising the steps of determining one or more plant types having enhanced production of phytolithic organic carbon and cultivating the one or more plant types at a location or region to increase the phytolithic organic carbon production at the location or region.

The method of the fifth aspect may further involve the step of replacing existing growing biomass at the location or region with the one or more plant types having enhanced production of phytolithic organic carbon. By "enhanced production of phytolithic organic carbon", it is meant that the production of phytolithic organic carbon by the one or more plant types is higher than for the existing plant types growing at the location or region. Most native grasses, wetland herbaceous plants such as giant rush, *cyperaceae* species and domesticated plants such as barley, corn, rice, sugar cane and wheat, have high levels of phytoliths.

Other plants have high phytolithic content but the occluded carbon within the phytoliths has not been calculated, these plants are listed below (taken from J. F. Parr, L. A. Sullivan, Soil Biology and Biochemistry 37 (2005): 117-124 121).

Abundance of Extracted Phytoliths from Herbarium Specimens Assessed Visually on Glass Slides at 400× Magnification from Plant Species Occurring at Numundo and Byron Bay Sites High Asteraceae: *Vernonia cinerea* (L.) *Less., Blechcaceae: Blechnum indicucm Burm. F., Cyperaceae: Gahnia sieberana Kunth., Moraceae: Artocarpus cumingiana Trec., Ficus coronata Spin., Myrtaceae: Eucalyptus robusta* Smith, *Pandanaceae: Pandanus tectorious Solms., Poaceae: Bambusa forbesii* (Ridl.) *Holttum, Brachiaria brizantha* (Hoscht. Ex A. Rich) *Stap f., Buergersiochloa macrophylla* S. T. Blake, *Blumea Supp., Coix lachryma-jobi* L., *Hetaropogon triticus* (R.Br) *Stapf.* Ex *Cralb, Imperata cylindrica P. Beauv., Imperata exaltata* (Roxb.) *Brogn., Ischaemum polystachyum* (L.), *Polytoca macrophylla Benth., Saccharum officinaruni* (L.), *Saccharum robustum* (L.), *Seteria sphacelata* (K. Schum.) *Stapf.* & C. E. Hubb, *Schizostachym brachycladum* (Blanco) *Mer., Themeda arguens* (L.) Hack, *Thysanolsara maxima* (Roxb.) O.K., *Pteridophyta: Diplazium esculentum* (Retz.) *Sw., Rubiaceae: Massaenda ferruginea K. Sch.* Var. *scandens Val., Timonius* sp., *Scrophulariaceae: Buchnera tumentosa Bl., Simaroubaceae: Ailanthus integrifolia Lamk.*

Medium

Annonaceae: *Annona muricata* L., Arecaceae: *Areca catachu* L., *Caryota rumphiana* Mart., *Cocas nucifera* L. Burseraceae: *Canarium indicum* L., Combretaceae: *Terminalia catappa* L., Cucurbitaceae: *Bryophyllum pinnatum* (Lamk) Kurz., *Luffa cylindrica* (L.) Roem., Cyperaceae: *Cyperus kyllingia* Endl., Moraceae: *Ficus nodosa* Teysm. & Binn, *Ficus papus* Peekel, *Ficus pungens* Reinw. ex Bl., Myrtaceae: *Eucalyptus maculata* Hook., *Leptosperimum* sp., Piperaceae: *Piper betal* L., Pteridophyta: *Nephrolepis hirstulata* (Forst.) Presl, Rubiaceae: *Massaenda ferruginea* K. Sch. Var. *scandens* Val., Rutaceae: *Euodia hortensis* J.R.&G. Forst., Sapotaceae: *Burckella obovata* (Forst.) Pierre, Simaroubaceae: *Quassia indica* (Gaertn.) *Nooteboom*

Low

Acanthaceae: *Hemigraphis reptans* (Forst. F.) *And.* ex Hemsley, Amaranthaceae: *Cyathula prostrata* Bl., Anarcardiaceae: *Dracontomelon dao* (Blanco) Merr & Rolfe, *Spondias dulcis* Soland. ex Forst., Annonaceae: *Cananga odorata* Hook., Apocynaceae: *Alstonia scholaris* R. Br., *Cerbera manghas* L., *Ichnocarpus frutescens* (L.) R. Br., Araceae: *Colocasia esculenta* (L.) Schott., *Schismatogloftis calyptrata* (Roxb.) Zol & Mor., *Pothos helwigii* Engl., Araliaceae: *Polyscias cummingiana* (Presl.) F.-Vill., Arecaceae: *Licuala peckelii* Laut., *Metroxylon sagu* Roftb., *Nypa fruticans* Wurnb., Aristolochiaceae: *Aristilochia tagala* Cham., Barringtoniaceae: *Barringtonia asiatica* L., *Barringtonia novae-hiberniae* Laut., Boraginaceae: *Cordia subcordia* Lanik., Caryophyllaceae: *Drymaria cordata* (L.) Willd. Ex Roem & Schult., Convolvulaceae: *Ipomea batatus* L., *Ipomea congesta* R. Br., Cycadaceae: *Cycus rumphii* Miq., Cyperaceae: *Mapanea macrocephala* (Gaud.) K. Sch., Dioscoreaceae: *Dioscorea pentaphylla* L., Ebenaceae: *Diospyros peekelii* Laut., Euphorbiaceae: *Macaranga aleuritoides* F. Muell., *Macaranga tararius* (L.) Muell.-Arg., *Macaranga urophylla* Pax & Hoffm., *Manihot esculenta* Crantz., Fabaceae: *Canavalia rosea* (Sw.), *Casia alata* L., Flagallariaceae: *Flagallerea gigantia* Hook. f., *Flagallarea*

*indica* L., Flacourtiaceae: *Homalium foetidum* (Roxb.) Benth., *Pangium edule Reinw.*, Gnetaceae: *Gnetum gnemon* L., *Gnetum latifolium* L., Goodeniaceae: *Scaevola taccada* (Gaertn.) Roxb., Hemandiaceae: *Hemandia nyniphaefolia* (presl) *Kubitski*, Lamiaceae: *Ocimum basilicum* L., Lauraceae: *Cassytha filiformis* L., *Litsea grandiflora Teschn.*, Liliaceae: *Cordyline fruiticosa* (L.) A. Chev., *Cordyline terminalis Kunth*, Malvaceac: *Hibiscus manihot* L., *Hibiscus tiliaceus* L., *Sida rhombifolia* L., Marantaceae: *Donax canniformis* (Forst.) *K. Sch.*, Melastomataceae: *Osbeckia chinensis* L., Moraceae: *Artocarpus cumingiana Trec.*, Musaceae: *Heliconia bihai L., Heliconia indica Lamk., Musa accuminata* (simons), *Musa becarrii* (simons), *Musa erecta* (simons), *Musa paradisica* L., *Musa peekellii Laut., Musa schizocarpa* (simons), *Musa truncata* var. *horizontalis* Holtlum., *Ensete calosperma F.U.M.*, Myrtaceae: *Syzigium bevicymum* (Diels) Merr. & Perry *Syzigiummalaccence* (L.) Merr. & Perry, Nyctaginaceae: *Pisonia longirostris* Teys. & Binn., Orchidaceae: *Dendrobium bifalce Lindl., Dendrobium peekelii schltr.*, Piperaceae: *Piper mestorii* F. M. Bail., *Piper peekelii C. DC.*, Pittosporaceae: *Pitosporum ferrugineum Ait.*, Podocarpaceae: *Dacrycarpus imbricatus Bl.*, Proteaceae: *Banksia* sp., Pteridophyta: *Bolbitis quogana* (Gaud.) Ching, Rhamnaceae: *Alphitonia macrocarpa Mansf., Alphitoria molaccana* Reiss. ex Endl., Rhizophoraceae: *Brugiera gymnorrhiza* (L.) Lamk, *Rhizophora apiculata Bl.*, Rosaceae: *Cyolendophora laurina* (A. Gr.) Kosterm., *Rubus rosaefolius* Sm., Rubiaceae: *Uncaria bernaysii F. Muell.*, Sapindaceae: *Pometia pinnarta* J. R. & G. Forst., Scrophulariaceae: *Lindernia crustaccae* (L.) F. Muell., Solanaceae: *Datura metal* L., *Solanum erianthum* D. Don., *Solanum torvum* Sw., Sterculiaceae: *Heritiera littoralis Dryand* ex W. Ait., *Kleinhohia hospita L., Melochia odorata L. f.*, Urticaceae: *Dendrocnide warburgii* (Winkl.) Chew, *Leukosyke capitellata Poir., Pipturus argenteus* (Forst.) Wedd., Verbenaceac: *Premna serratifolia* L., Xanthorrhoeaceae: *Xanthorrhoea resinosa* Pers. High: >66% cover of slide, Medium: >33 to <66% cover, and Low: >1 to <33% cover.

In a sixth aspect, the present invention provides a method for determining carbon credits comprising:

a) determining one or more varieties of plants that can be used to enhance phytolithic organic carbon production;

b) establishing phytolithic organic carbon sequestration data for the one or more varieties of plants under environment conditions appropriate to a selected location;

c) arranging cultivation of at least one of the varieties of plants in the location; and d) determining carbon credits on the basis of the phytolithic organic carbon sequestration data and cultivation practice.

This aspect may also involve breeding varieties of plants that can be used to enhance phytolithic organic carbon production. In the context of this specification, breeding of plants includes conventional plant breeding techniques, genetic manipulation techniques, tissue culture techniques and indeed any other technique that results in new varieties of plants being developed.

In a seventh aspect, the present invention provides a method for claiming carbon credits including the steps of:

a) determining an amount of phytolithic organic carbon arising from vegetative biomass growing on a location or region;

b) determining an amount of phytolithic organic carbon arising from cultivation of one or more plants having enhanced production of phytolithic organic carbon on the location or region;

c) cultivating the one or more plants having enhanced phytolithic organic carbon on the location or region; and d) claiming a carbon credit based upon the difference between the amount determined in step (b) and step (a).

Step (a) suitably determines an amount of phytolithic carbon produced by the vegetative biomass growing at the selected location or region in a specified period of time. For example, in low lying wetlands around the Byron Bay area of Australia, the present inventors have established that the natural vegetation sequesters carbon at a rate of $0.9$ $gCm^2$ per year. Step (b) suitably determines an amount of phytolithic organic carbon arising from cultivation of one or more plants having enhanced production of phytolithic organic carbon at the selected location or region in a similar period of time. A claim for carbon credits can be made where the amount determined in step (b) is larger than the amount determined in step (a).

In an eighth aspect, the present invention provides a method for claiming carbon credits using formula (1):

$$A = B_1 - B_2 \quad (1)$$

where:

A=an amount of carbon that is claimed as a carbon credit from cultivating a particular plant type in a specified location or region;

$B_1$=an amount of carbon sequestered in phytoliths produced by the plant type at that selected location or region in a specified period of time; and $B_2$=an amount of carbon sequestered in phytoliths prior to the cultivation of that plant type at that selected location or region in a similar period of time.

Where $B_1$ exceeds $B_2$, a carbon credit can be claimed.

In this aspect of the present invention, cultivation of the plant type includes one or more of the following: choice of plant type or cultivar, the addition of amendments to improve growth rate of the plant type, intensive growing of the plant type, growing of the plant type under artificial conditions (such as in a greenhouse, using hydroponics, using an aquaculture method, etc.) or any other practice aimed at effecting or increasing the amount of phytolithic carbon sequestration.

In this aspect of the present invention, $B_1$ may be calculated in accordance with formula (2) below:

$$B_1 = (\text{PhytOC yield}) \times (\text{vegetative biomass production}) \quad (2)$$

where:

PhytOC yield=the proportion of biomass of the plant type that exists as phytolithic organic carbon during the specified period of time; and vegetative biomass production=the amount of vegetative biomass produced during the specified period of time.

The PhytOC yield could be either determined directly for a specified time period for a selected location or region by any of the methods described herein above in this specification. Alternatively, it may be estimated using previous PhytOC data for the specified plant type.

$B_2$ may be calculated in accordance with formula (3):

$$B_2 = (\text{previous PhytOC yield}) \times (\text{previous vegetative biomass production}) \quad (3)$$

where:

previous PhytOC yield=the proportion of vegetative biomass of the previously cultivated plant type(s) that existed as phytolithic organic carbon; and previous vegetative biomass production=the amount of vegetative biomass produced prior to the cultivation of that plant type at that selected location or region in a similar period of time.

$B_2$ is the amount of carbon sequestered in phytoliths and can be determined (1) from that which existed prior to the cultivation of a plant type (either by determination or estimation) or (2) using an estimated global average PhytOC for vegetation (which is approximately 0.9 gCm$^2$ per year as determined by the present inventors).

In a ninth aspect, the present invention provides a method for sequestering carbon including the steps of a) treating vegetative biomass to produce a mass containing phytoliths;

b) sequestering the phytoliths by using the mass produced in step (a) as a landfill, a road base or as a component in a manufacturing process;

c) determining the carbon content of the phytoliths in the mass; and d) claiming a carbon credit based upon the determined carbon content.

Step (a) may comprise simply harvesting growing plants, or it may also comprise further treatment of harvested plants. For example, the further treatment may include low temperature combustion to produce an ash containing phytoliths. Alternatively, it may comprise an acid digestion or microwave digestion to extract phytoliths from the vegetative biomass.

Step (b) may comprise placing the mass containing the phytoliths into a landfill and, optionally, covering the mass with soil or other waste disposed in the landfill. Alternatively, the mass may be used as a component in a road base material. This is effective in locking up the phytoliths because the road base material is covered by bitumen, asphalt or concrete during construction of the road. As a further alternative, the mass of material containing the phytoliths may be used as a component in a manufacturing process. Some examples of suitable manufacturing processes include cement manufacture, concrete manufacture, manufacture of building materials such as clay bricks, concrete bricks, sheeting material or other building material.

Government regulations or international treaties relating to claiming carbon credits may require that carbon sequestration for a location or region be determined at a specified starting date (for example, the UNFCCC currently specifies 1990 as a start date), determining carbon sequestration at a later date, with any difference in carbon sequestration leading to the claim for a carbon credit. Accordingly, the step of determining a carbon credit in the various aspects of the present invention may include the step of determining carbon sequestration arising from PhytOC at the location or region at a specified start date and subtracting that from the determined carbon sequestration arising from PhytOC at the location or region at a later date.

It will also be realised that other factors besides PhytOC sequestration may be included in the calculation of a carbon credit, for example, carbon taken out of the atmosphere by additional vegetative biomass growing at the location or region. Thus, the carbon credit claimed by virtue of PhytOC sequestration may form but a part of an overall carbon credit claim.

The carbon credits may be traded as desired. Thus, the present invention also includes trading systems and methods for trading carbon credits calculated in accordance with the various aspects of the present invention.

The methods of the present invention that relate to determining carbon credits are based on recognising the concept that carbon sequestration in phytoliths can be validated, quantified and applied to an agricultural based business whereby useful economic benefits to the operator of the agricultural business can be substantiated. In some aspects, the concept includes establishing the phytoliths in soil or plant material in a validated manner whereby an economic benefit in terms of a claim for carbon credits can be made.

Preferred embodiments of some aspects of the invention are those where validated data is developed to establish optimal or near optimal agricultural operations to predict carbon sequestration based on historical data or by analysis.

In preferred embodiments of some aspects of the invention, the method includes making a claim for carbon credits based on the data for carbon sequestration related to the plant type and to the location at which the plant type is growing or is to be grown. Validation of the carbon credit claim may take into account specific growing conditions and, where possible and relevant, include modifying the growing conditions, for example, by alteration of moisture levels, pH and/or fertiliser regimes towards optimising phytolithic carbon development in the plant structure.

In some aspects, the methodology of the present invention may include further validating measurements in relation to a growing cycle to establish biomass generated and phytolithic carbon sequestration to further authenticate and validate the claim.

It is acknowledged that natural environments such as forest and, in particular, rainforests, will sequester carbon, some of which is in the phytolithic and therefore secure sequestered form. However, the inventors point out that other species, notably grass crop species including wheat, are grown most extensively for food production and point out the considerable efficiency of these species in producing phytolithic organic carbon. The inventors point out that the role of biogenic silica phytoliths in carbon storage and its validity to carbon sequestration and carbon credit claims has been overlooked. Based on this realisation the inventors propose optimisation of agricultural business approaches to establish and preferably optimise carbon sequestration for economic benefits.

The inventors' investigations demonstrate that particular types of habitats and plant species produce different quantities of phytoliths under various conditions. Data has been currently accrued for coastal plains, foreshore areas, rainforest, peatlands, wetlands and woodland habitats under a range of conditions from the wet tropics of Papua New Guinea, the Torres Strait Islands, coastal northern New South Wales and its hinterland. Results showing that of an initial 81 plant families comprising 213 species tested some 59 families and c. 100 species were found to have diagnostic phytoliths types that did not overlap in morphology with each other.

Furthermore the inventors have established that the above habitats and plant species retain variable amounts of carbon (PhytOC) within the phytoliths they produce (Tables 1 & 2). Thus from the data, favourable conditions for phytolith production and therefore carbon sequestration can be calculated for specific types of land.

Once a phytolith is isolated from the surrounding plant material and is buried in nature it is resistant to deterioration and can retain the sequestered carbon for periods exceeding 8,000 years. Thus the inventors have demonstrated through field and laboratory experiments that carbon can be sequestered in a range of natural environments as PhytOC. Where such environments are human induced under the most optimal conditions, phytolith yield and in particular PhytOC can be predicted and ultimately exploited. This follows from traditional farming practice where optimal conditions are observed from nature and manipulated to enhance exploitation of a given crop.

TABLE 1

Summary of various habitats with the same annual rainfall, various soil pH levels, different dominant plants species within these habitats and the calculated carbon sequestered in the phytolith content extracted from 0.25 grams of soil from each habitat.

| Habitat | annual rainfall | soil pH | Dominant plant family | % PhytOC |
|---|---|---|---|---|
| Open coastal grassland | 4,000 mm | 4.87 | Poaceae | 0.5105 |
| Open grassland | 4,000 mm | 6.43 | Poaceae | 0.4424 |
| Disturbed herbaceous wetland | 4,000 mm | 6.96 | Amaranthaceae | 0.1900 |
| Herbaceous wetland | 4,000 mm | 6.69 | Cyperaceae | 0.2873 |
| Peatland | 4,000 mm | 3.68 | Restionaceae | 5.0535 |

TABLE 2

Example of phytolith carbon content from rice *Oryza sativa* and spinifex grass *Triodia reptins* extracted from plant material using microwave digestion and analysed by LECO total carbon analysis.

| Species | % PhytOC |
|---|---|
| *Oryza sativa* | 0.9 |
| *Triodia reptins* | 1.0 |

Those skilled in the art will appreciate that the present invention may be subject to variations and modifications other than those specifically described. It is to be understood that the present invention encompasses all such variations and modifications that fall within its spirit and scope.

The invention claimed is:

1. A method for determining the phytolithic organic carbon yield of a plant type at a location or region comprising:
    a) taking a sample of a plant type growing the location or region;
    b) extracting phytoliths from the sample;
    c) quantifying phytolithic organic carbon in the sample;
    d) quantifying a total biomass of the plant type growing at the location or region; and
    e) determining a total amount of phytolithic organic carbon for the total biomass of the plant type at the location or region.

2. The method as claimed in claim 1, wherein the method comprises taking samples of a plurality of plant types growing in the region or location, quantifying phytolithic organic carbon in the sample of each plant type, quantifying a total biomass of each of the plant types growing at the location or region and determining a total amount of phytolithic organic carbon for the total biomass of the plant types at the location or region.

3. The method as claimed in claim 1, wherein the total biomass of the plant type is determined by a technique selected from the group consisting of direct sampling, indirect measurement using harvest data and known harvest indices, remote sensing techniques and using biomass accumulation curves.

4. A method for determining a carbon credit including the steps of:
    a) taking a sample of a plant type growing in a location or region;
    b) extracting phytoliths from the sample;
    c) quantifying phytolithic organic carbon in the sample;
    d) quantifying a total biomass of the plant type at the location or region;
    e) determining a total amount of phytolithic organic carbon for the total biomass of a plant type at the location or region; and
    f) determining a carbon credit applicable to the location or region based upon the total amount of phytolithic organic carbon determined in step (e) above, wherein the carbon credits are equal to phytolithic organic carbon yield multiplied by the total biomass, wherein the phytolithic organic carbon yield is the proportion of the total biomass of the plant type that exists as phytolithic organic carbon.

5. The method as claimed in claim 4, wherein the method comprises taking samples of a plurality of plant types growing in the region or location, quantifying phytolithic organic carbon in the sample of each plant type, quantifying a total biomass of each of the plant types growing at the location or region, determining a total amount of phytolithic organic carbon for the total biomass of the plant types at the location or region and claiming a carbon credit based upon the total amount of phytolithic organic carbon.

6. The method as claimed in claim 4, wherein the location or region is subjected to cultivation or agriculture, in which crops of the plant type are periodically grown at regular intervals and the total phytolithic organic carbon present in the crop represents a cumulative total of carbon permanently sequestered from the atmosphere for each cropping cycle and a carbon credit equivalent to the phytolithic organic carbon total of the crop minus that which would have been sequestered had the crop not been cultivated is claimed for each cropping cycle.

7. The method as claimed in claim 4, wherein the location or region is not subjected to regular cropping and the increase in the total amount of phytolithic organic carbon arising from the increase in biomass on the location or region due to plant growth over a period of time is claimed as a carbon credit.

8. A method for determining the phytolithic organic carbon accumulating at a location over a period of time comprising the steps of:
    a) collecting a sample of material from the ground at the location;
    b) extracting phytoliths from the sample;
    c) determining the phytolithic organic carbon content of the material;
    d) using data determined in step (c) above, determining a total phytolithic organic carbon content in the material at the location;
    e) after a predetermined period of time has elapsed, collecting a further sample of material Thorn the ground at the location;
    f) extracting phytoliths from the sample;
    g) determining a phytolithic organic carbon content of the material in the sample;
    h) determining a total phytolithic organic carbon content in the material at the location from the data determined in step (g) above; and
    i) determining an amount of phytolithic organic carbon that has accumulated at the location over the predetermined time interval by subtracting the amounts determined in step (d) from the amount determined in step (h).

9. The method as claimed in claim 8, wherein the material collected from the ground preferably includes leaf litter, humus and at least an upper layer of the soil.

10. The method as claimed in claim 1 further comprising calculating a carbon credit from the determined amount of phytolithic organic carbon.

11. The method as claimed in claim 4 further comprising the step of determining the amount of carbon sequestration arising from PhytOC at the location or region at a specified start date and subtracting that from the determined amount of carbon sequestration arising from PhytOC at the location or region at a later date.

12. The method as claimed in claim 4, wherein the carbon credit claimed by virtue of PhytOC sequestration forms but a part of an overall carbon credit claim.

* * * * *